US011076964B2

(12) United States Patent
Mimnaugh et al.

(10) Patent No.: US 11,076,964 B2
(45) Date of Patent: Aug. 3, 2021

(54) METARSOPHALANGEAL JOINT REPLACEMENT DEVICE AND METHODS

(71) Applicant: Zimmer, Inc., Warsaw, IN (US)

(72) Inventors: Kimberly Mimnaugh, Warsaw, IN (US); Oludele O. Popoola, Granger, IN (US); Jeremy Edward Phillips, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 138 days.

(21) Appl. No.: 16/553,559

(22) Filed: Aug. 28, 2019

(65) Prior Publication Data

US 2020/0069434 A1 Mar. 5, 2020

Related U.S. Application Data

(60) Provisional application No. 62/724,273, filed on Aug. 29, 2018.

(51) Int. Cl.
*A61F 2/42* (2006.01)
*A61F 2/30* (2006.01)

(52) U.S. Cl.
CPC .......... *A61F 2/4225* (2013.01); *A61F 2/3094* (2013.01); *A61F 2/4241* (2013.01);
(Continued)

(58) Field of Classification Search
CPC .................. A61F 2/4225; A61F 2/4241; A61F 2002/4233; A61F 2002/4228; A61F 2002/4238; A61F 2002/4251
See application file for complete search history.

(56) References Cited

U.S. PATENT DOCUMENTS 3,593,342 A 7/1971 Niebauer et al.
3,886,600 A 6/1975 Kahn et al.
(Continued)

FOREIGN PATENT DOCUMENTS

CN 1486166 3/2004
CN 103189018 7/2013
(Continued)

OTHER PUBLICATIONS

"European Application Serial No. 19194431.3, Partial Supplementary European search report dated Jun. 24, 2020", 12 pages.
(Continued)

*Primary Examiner* — David H Willse
*Assistant Examiner* — Javier G Blanco
(74) *Attorney, Agent, or Firm* — Schwegman Lundberg & Woessner, P.A.

(57) ABSTRACT

A device for the repair of a phalangeal joint comprises a first anchor, a second anchor, and a flexible spacer connecting the first and second anchors. The flexible spacer comprises a plurality of elongate fibers extending axially or criss-crossed between the first and second anchors and a polymeric matrix interspersed with the plurality of elongate fibers. Specifically, a prosthetic metatarsophalangeal joint device comprises a porous metallic metatarsal bone anchor, a porous metallic phalangeal bone anchor, and a polymeric spacer element comprising parallel or criss-crossed elongate fibers that can connect the metatarsal bone anchor and the phalangeal bone anchor. Methods for manufacturing prosthetic joint devices comprise using three-dimensional printing processes or molding processes. Methods for implanting prosthetic joint devices comprise positioning porous metallic anchor components adjacent resected bones at planar interfaces and between which a polymeric spacer having
(Continued)

axial aligned elongate fibers embedded in a matrix can be disposed.

10 Claims, 9 Drawing Sheets

(52) U.S. Cl.
CPC ............ *A61F 2002/30009* (2013.01); *A61F 2002/3097* (2013.01); *A61F 2002/30968* (2013.01); *A61F 2002/30985* (2013.01); *A61F 2002/4228* (2013.01); *A61F 2002/4233* (2013.01); *A61F 2002/4238* (2013.01); *A61F 2002/4251* (2013.01); *A61F 2310/00023* (2013.01); *A61F 2310/00029* (2013.01)

(56) References Cited

U.S. PATENT DOCUMENTS

| | | | |
|---|---|---|---|
| 5,480,447 A | 1/1996 | Skiba | |
| 5,879,396 A * | 3/1999 | Walston | A61L 27/16 623/23.41 |
| 6,007,580 A | 12/1999 | Lehto et al. | |
| 8,920,453 B2 | 12/2014 | Tyber et al. | |
| 9,907,663 B2 | 3/2018 | Patrick et al. | |
| 2003/0097180 A1 | 5/2003 | Tormala et al. | |
| 2005/0116400 A1* | 6/2005 | White | A61F 2/442 267/158 |
| 2009/0157181 A1* | 6/2009 | Osman | A61F 2/28 623/16.11 |
| 2017/0367838 A1 | 12/2017 | Cavanagh et al. | |
| 2018/0161170 A1 | 6/2018 | Petranto | |

FOREIGN PATENT DOCUMENTS

| | | |
|---|---|---|
| CN | 110870812 | 3/2020 |
| EP | 0042808 | 12/1981 |
| EP | 0057597 | 8/1982 |

OTHER PUBLICATIONS

"Chinese Application Serial No. 201910806027.2, Office Action dated May 7, 2021", with English translation, 17 pages.

"European Application Serial No. 19194431.3, Extended European Search Report dated Sep. 28, 2020", 11 pages.

* cited by examiner

METATARSOPHALANGEAL JOINT REPLACEMENT DEVICE AND METHODS

CLAIM OF PRIORITY

This application claims the benefit of U.S. Provisional Patent Application Ser. No. 62/724,273, filed on Aug. 29, 2018, the benefit of priority of which is claimed hereby, and which is incorporated by reference herein in its entirety.

TECHNICAL FIELD

The present application relates generally to prosthetic implants for joints of a foot or hand. More specifically, the present application relates to flexible cartilage replacement devices that can be attached between two bones, as can be used in methods for arthroplasty of an interphalangeal joint, such as a metatarsophalangeal or metacarpalphalangeal joint.

BACKGROUND

Wearing down or wearing out of cartilage between bones of a joint can be characterized as osteoarthritis ("OA"). OA in the main joint of the great toe (i.e., the first metatarsophalangeal joint ("MTPJ1") can cause sometimes unbearable pain and discomfort in a patient. A variety of metatarsophalangeal joint replacement devices have been developed for use in the first metatarsophalangeal joint (MTPJ1).

An example of a metatarsophalangeal joint replacement device rigidly connected components that are implanted between opposing bones of a joint in the intramedullary area of each bone. In such a configuration, the bones are typically fused together. An example of such a device is described in detail in U.S. Pat. No. 8,920,453 to Tyber et al.

Another type of metatarsophalangeal joint replacement device utilizes a pair of components that are implanted into opposing bones to abut each other. The components are configured to slide against each other to produce an articulating joint that is non-fused. An example of such a device described in detail in U.S. Pub. No. 2017/0367838 to Cavanagh et al.

Another type of metatarsophalangeal joint replacement device utilizes a pad or cushion inserted between the bones. The pad or cushion is typically attached via intramedullary inserts that extend into the opposing bones. Examples of such devices are described in detail in U.S. Pat. No. 5,480,447 to Skiba, U.S. Pat. No. 5,879,396 to Walston et al. and U.S. Pat. No. 6,007,580 to Lehto et al.

Another type of metatarsophalangeal joint replacement device utilizes a pad or cushion that is positioned between the bones in substitution of the cartilage and can be connected to the bones by minimally invasive means. An example of such a device described in detail in U.S. Pat. No. 9,907,663 to Patrick et al.

Issues in conventional metatarsophalangeal joint replacement devices persist and can cause discomfort for patients. There is, therefore, a need for interphalangeal, e.g., metatarsophalangeal, joint implants that reduce or eliminate pain, provide better comfort and performance for the patient.

OVERVIEW

The present inventors have recognized, among other things, that problems to be solved in MTPJ1 devices can include being too stiff, feeling too loose, over-intrusive implantation, and inadequate coupling to the bone. Conventional MTPJ1 devices can thus feel unnatural to the patient. Some conventional metatarsophalangeal joint replacement devices typically result in fusing of the joint, which causes stiffness in the joint and discomfort for the patient. Even when not fused, these devices may feel too tight (difficult to bend) or too loose (joint hypermobility as in Ehlers-Danlos syndrome: the joint unnaturally separates) to the patient and the implants may loosen due to inadequate fixation to the bone. Some devices also may require extensive intramedullary implantation into both bones of the joint, which can complicate the arthroplasty procedure.

In particular, polymeric or hydrogel pads or spacers inserted between the metatarsal bone and the phalange bone can be too stiff to reproduce natural flexion. Additionally, it can be difficult for these types of spacers to attach to the bone. For example, the spacer provides a small footprint for the facilitation of bone in-growth or the adhesion of bone cement, which can be difficult to deliver to the joint in the desired location.

The present subject matter can help provide a solution to these and other problems, such as by providing an interphalangeal joint device, such as an MTPJ1 device that can firmly attaches to the metatarsal (or metacarpal) bone and the phalange bone without requiring intrusive, intramedullary operations, while also providing a degree of flexibility and tightness that can more closely replicate the natural joint, thereby providing better patient comfort and performance. Furthermore, devices of the present disclosure can be manufactured in configurations that are simple to implant and that can be readily customized.

In an example, a device for the repair of a phalangeal joint can comprise a first anchor, a second anchor, and a flexible spacer. The flexible spacer can connect the first anchor and the second anchor, and can comprise a plurality of elongate fibers extending, axially or criss-crossed between the first and second anchors, and a polymeric matrix interspersed with the plurality of elongate fibers.

In another example, a prosthetic metatarsophalangeal joint device can comprise a metatarsal, or metacarpal, bone anchor that can comprise a porous metallic material, a phalangeal bone anchor that can comprise a porous metallic material, and a polymeric spacer element that can connect the metatarsal bone anchor and the phalangeal bone anchor. The polymeric spacer element can comprise a plurality of elongate fibers extending, parallel or criss-crossed, between the metatarsal bone anchor and the phalangeal bone anchor.

In an additional example, a method of manufacturing a device for the repair of a phalangeal joint can comprise fabricating first and second anchor components using a first additive manufacturing process (e.g., 3D printing) to produce a porous structure within each component, fabricating a flexible spacer component using a second additive manufacturing process or molding process to produce a plurality of elongate fibers extending straight across or criss-crossed through the flexible spacer, and attaching opposing ends of the flexible spacer component to the first and second anchor components.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
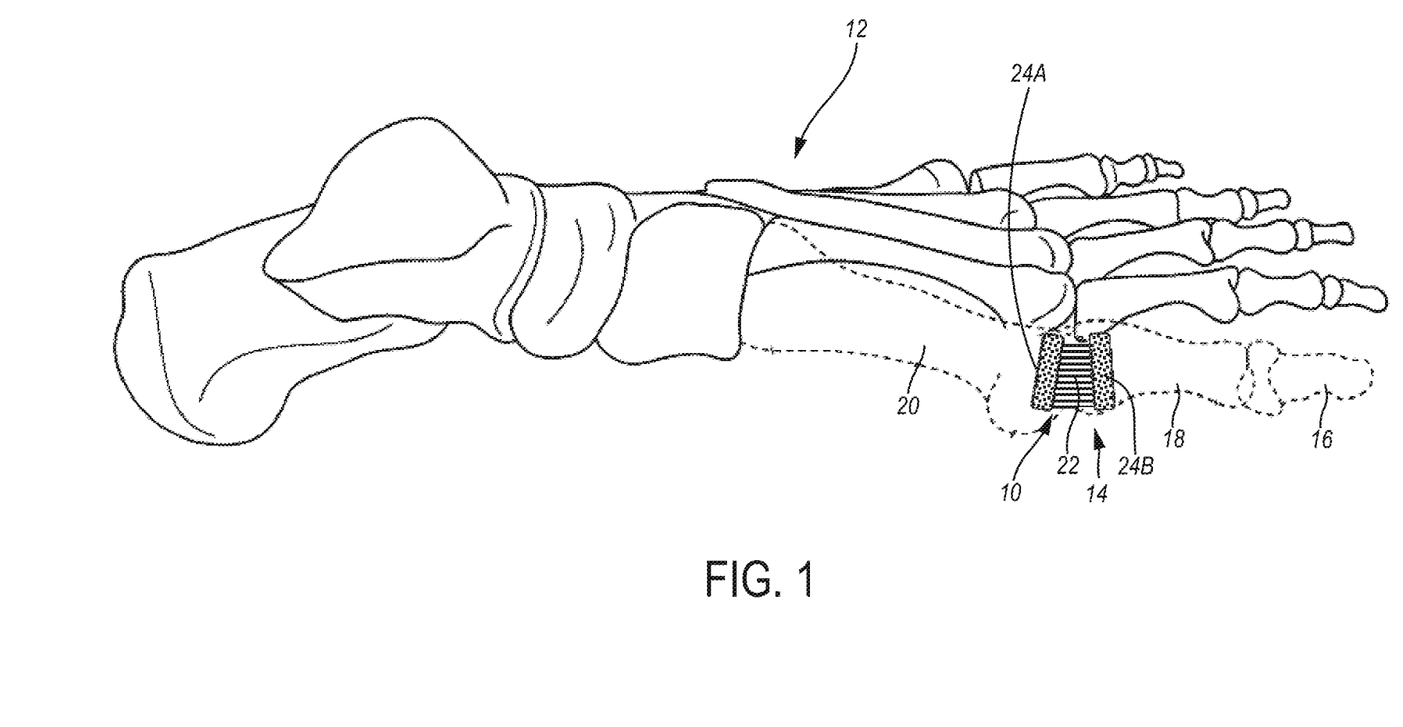
FIG. 1 is a diagram illustrating a prosthetic joint device of the present disclosure implanted in a first metatarsophalangeal joint of a foot.

FIG. 1 is a diagram illustrating prosthetic joint device 10 implanted in foot 12 at first metatarsophalangeal joint (MTPJ1) 14. Foot 12 includes five digitorum bones that each include one or both of a distal and medial phalange bone, a proximal phalange bone and a metatarsal phalange bone. For example, first metatarsophalangeal joint 14 includes distal phalange bone 16, proximal phalange bone 18 and metatarsal phalange 20. Prosthetic joint device 10 can include flexible spacer 22, first anchor component 24A and second anchor component 24B.

Prosthetic joint device 10 can be used to reproduce the natural or anatomic operation of a joint between two bones of foot 12. In the illustrated example, prosthetic joint device 10 is used in MTPJ1 14 between proximal phalange bone 18 and metatarsal phalange bone 20, but can be used in any of the digitorum bones of foot 12. Additionally, prosthetic joint device 10 can be used to repair or replace other small-bone joints, such as metacarpal joints of a hand.

Figure 6:
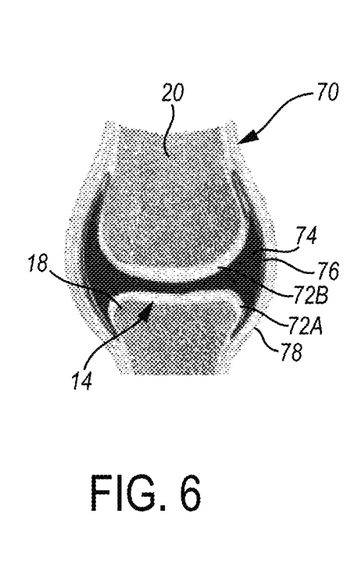
FIG. 6 is a diagram illustrating the anatomy of a first metatarsophalangeal joint.

A healthy anatomic MTPJ1 joint includes cartilage that the epiphysis end of each bone (see FIG. 6). The cartilage along with joint fluid provides a cushion between each bone that also facilitates flexion of the joint. The cartilage can become worn or can deteriorate with age, and trauma, thus causing pain and stiffness of the joint. Prosthetic joint device 10 can be implanted in the joint to alleviate the pain and restore proper joint flexibility and mobility. In particular, anchor components 24A and 24B can provide firm anchoring of prosthetic joint device 10 to bones 18 and 20 via osseointegration and flexible spacer 22 can hold MPJ1 14 joint together in the anterior-posterior direction while also providing flexion in a sagittal plane.

First anchor component 24A and second anchor component 24B can be attached to proximal phalange bone 18 and metatarsal phalange bone 20, respectively. In various examples, components 24A and 24B can be comprised of porous metallic material, such as porous titanium or tantalum. Flexible spacer 22 can be positioned between and connected to components 24A and 24B. In various examples, spacer 22 can comprise a polymeric component having anterior-posterior aligned fibers that can be embedded in a polymeric matrix to provide flexibility to the device.

Figure 2:
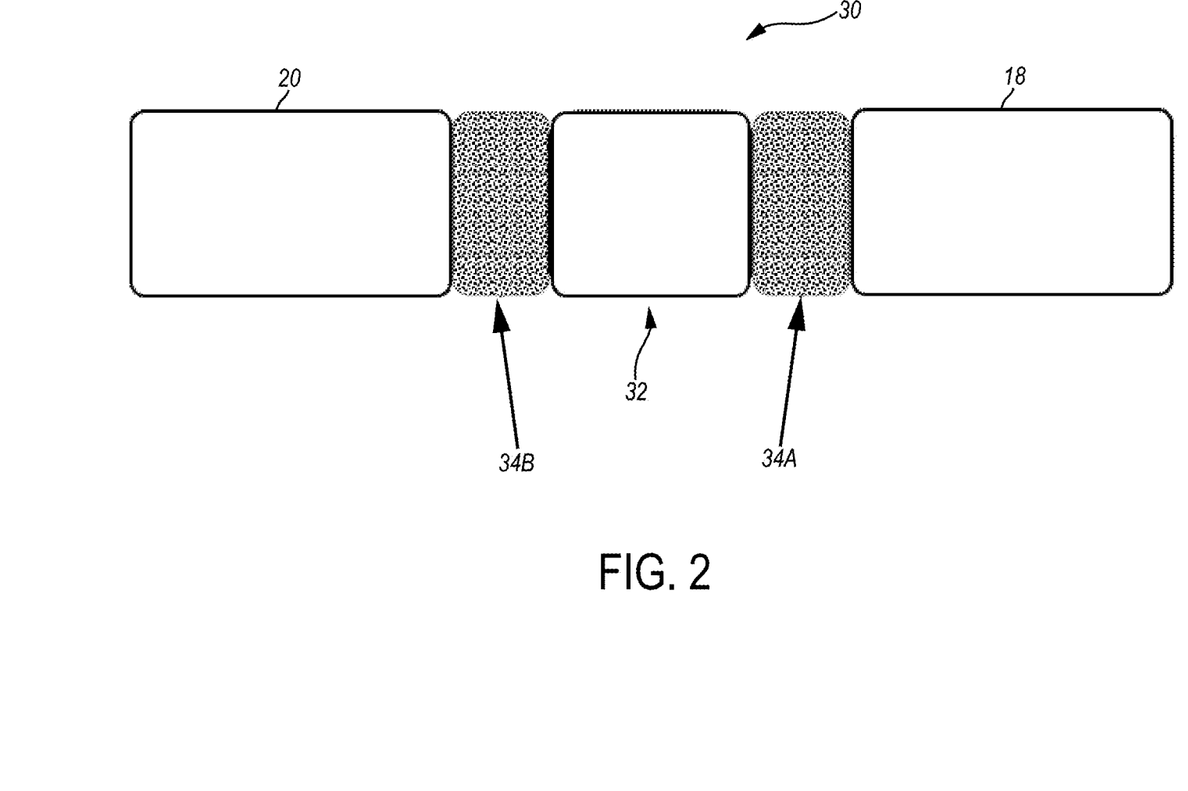
FIG. 2 is a schematic diagram illustrating a prosthetic joint device of the present disclosure including a flexible spacer connecting two anchor components positioned between opposing bones.

FIG. 2 is a schematic diagram illustrating prosthetic joint device 30 including flexible spacer 32 connecting first anchor component 34A and second anchor component 34B, which are connected to proximal phalange bone 18 and metatarsal phalange bone 20, respectively. In general, device 30, and other embodiments of the present application, can include two opposing anchor components, such as components 34A and 34B, that can be used to provide attachment to bone and a central cushion component, such as flexible spacer 32, that can provide coupling of and flexibility to the joint.

In an example, device 30 can be manufactured in multiple processes such that device 30 is a single integrated body of multiple materials. In such a configuration, flexible spacer 32 can be produced using an additive manufacturing process or molding process using a polymer, while anchor components 34A and 34B can be produced using a separate additive manufacturing process using a metal. However, in various examples, prosthetic joint device 30 can be comprised of a single monolithic structure or a plurality of different components attached together. Prosthetic joint device 30 can also be comprised of a single type of material or a plurality of material types. For example, device 30 can be manufactured in a single process such that device 30 is a monolithic body of only a polymeric material. In another example, device 30 can be manufactured using a single process such that device 30 comprises a monolithic body of multiple materials.

Figure 4:
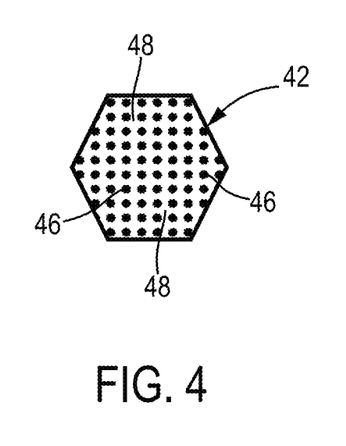
FIG. 4 is a cross-sectional view of the flexible spacer of FIG. 3 showing a plurality of polymer fibers disposed in a polymer matrix.
Figure 5:
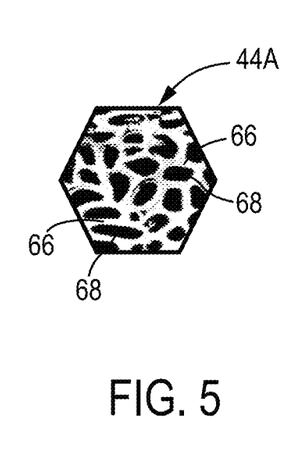
FIG. 5 is a cross-sectional view of an anchor component of FIG. 3 showing a metallic porous structure comprised of struts and voids.

Additive manufacturing processes, such as three-dimensional (3D) printing techniques, (such as electron beam or laser additive manufacturing) can be used to produce porous metallic structures of titanium alloys or tantalum, having geometries conducive to osteointegration and can additionally produce the intricacies of elongate fibers in a desired orientation. Furthermore, additive manufacturing processes allow one or more of the components of device 30 to be built directly onto one of more of the other components. As such, first anchor component 34A and second anchor component can be made of a porous metallic material to facilitate attachment to bone, while flexible spacer 32 can be made of a polymeric material including fibers to facilitate flexing. The specific shape and geometry of anchor components 34A and 34B and spacer 32 can vary based on design needs. For example, anchor components 34A and 34B and spacer 32 can have circular, rectangular, square or polygonal cross-sectional profiles. In an example, anchor components 34A and 34B and spacer 32 have hexagonal cross-sectional profiles, as shown in FIGS. 4 and 5. Hexagonal profiles can facilitate implantation into bone by providing adequate planar surface areas for bone contact and also providing edges for resisting rotation within the bone.

Figure 3:
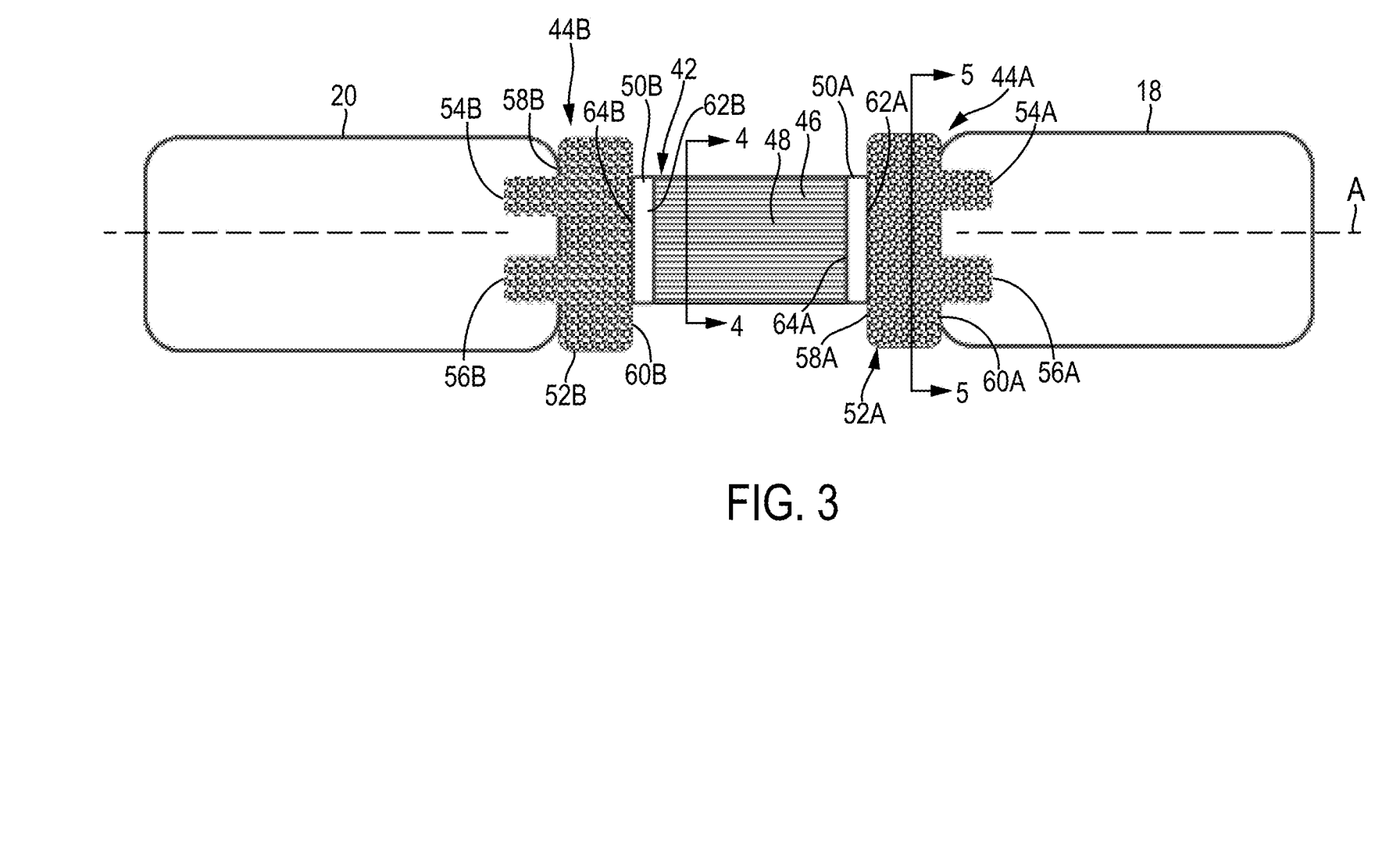
FIG. 3 is a schematic diagram illustrating another embodiment of a prosthetic joint device of the present disclosure including a flexible spacer comprising elongate fibers and anchor components including fixation pegs.

FIG. 3 is a schematic diagram illustrating prosthetic joint device 40 of the present disclosure including flexible spacer 42 and anchor components 44A and 44B coupled between proximal phalange bone 18 and metatarsal phalange bone 20. Flexible spacer 42 can comprise elongate fibers 46, matrix 48 and interdigitation zones 50A and 50B. Anchor component 44A can comprise base 52A and fixation pegs 54A and 56A. Anchor component 44B can comprise base 52B and fixation pegs 54B and 56B.

Base 52A of anchor component 44A can comprise a disk-like body for supporting flexible spacer 42 and facilitating attachment to proximal phalange bone 18. Posterior surface 58A can be flat or substantially flat to provide a base upon which interdigitation zone 50A can be located and built-up from. Likewise, anterior surface 60A can be flat to enhance bone contact with proximal phalange bone 18, which can be resected to provide a flat bone surface. Fixation pegs 54A and 56A can extend from anterior surface 60A in a location to allow fixation pegs 54A and 56A to be inserted into cancellous bone of proximal phalange bone 18. Fixation pegs 54A and 56A therefore increase the surface area of anchor component 44A in contact with bone to increase osseointegration, as well as provide initial fixation of anchor component 44A with bone 18.

Base 52B of anchor component 44B can comprise a disk-like body for supporting flexible spacer 42 and facilitating attachment to metatarsal phalange bone 20. Anterior surface 60B can be flat or substantially flat to provide a base upon which interdigitation zone 50B can be located and built-up from. Likewise, posterior surface 58B can be flat to enhance bone contact with metatarsal phalange bone 20, which can be resected to provide a flat bone surface. Fixation pegs 54B and 56B can extend from posterior surface 58B in a location to allow fixation pegs 54B and 56B to be inserted into cancellous bone of metatarsal phalange bone 20. Fixation pegs 54B and 56B therefore increase the surface area of anchor component 44B in contact with bone to increase osseointegration, as well as provide initial fixation of anchor component 44B with bone 20.

Anchor components 44A and 44B can be identical in geometry and can be interchangeable such that anterior surfaces 60A and 60B and posterior surfaces 58A and 58B can be reversed, respectively.

As discussed, bases 52A and 52B can have a variety of cross-sectional profiles. Additionally, the cross-sectional profiles of fixation pegs 54A, 56A, 54B and 56B can have a variety of cross-sectional profiles, such as circular, rectangular, square, polygonal, hexagonal and ribbed. As mentioned, posterior surface 58A and anterior surface 60B can be flat to facilitate adhesion with interdigitation zones 50A and 50B, respectively.

Interdigitation zones 50A and 50B can comprise solid bodies of material that can facilitate coupling of elongate fibers 46 to bases 52A and 52B, respectively. For example, interdigitation zone 50A can comprise a disk of material having anterior surface 62A that can be fused into pores of base 52A and posterior surface 64A from which fibers 46 can integrally extend. Likewise, interdigitation zone 50B can comprise a disk of material having posterior surface 64B that can be fused into pores of base 52B and anterior surface 62B from which fibers 46 can integrally extend.

Fibers 46 can extend from first interdigitation zone 50A to second interdigitation zone 50B. In an example, all of fibers 46 are parallel or substantially parallel to each other. Fibers 46 can extend parallel to axis A of device 40. Axis A can extend along the longitudinal centers of anchor components 44A and 44B, which can coincide with the anatomic centers of bones 18 and 20. Material of matrix 48 can be sandwiched between interdigitation zones 50A and 50B and filled-in between fibers 46. Material of matrix 48 can be in contact with fibers 46, but not bonded thereto. Coupling of interdigitation zones 50A and 50B to bases 52A and 52B, respectively, and fibers 46 provides axial, anterior-posterior stability and connection of device 40. Fibers 46 additionally permit flexible spacer 42 to bend as material of matrix 48 can slide past and around fibers 46 under deflection. As such, device 40 can replicate the feel and flexibility of an anatomic joint.

Figure 8:
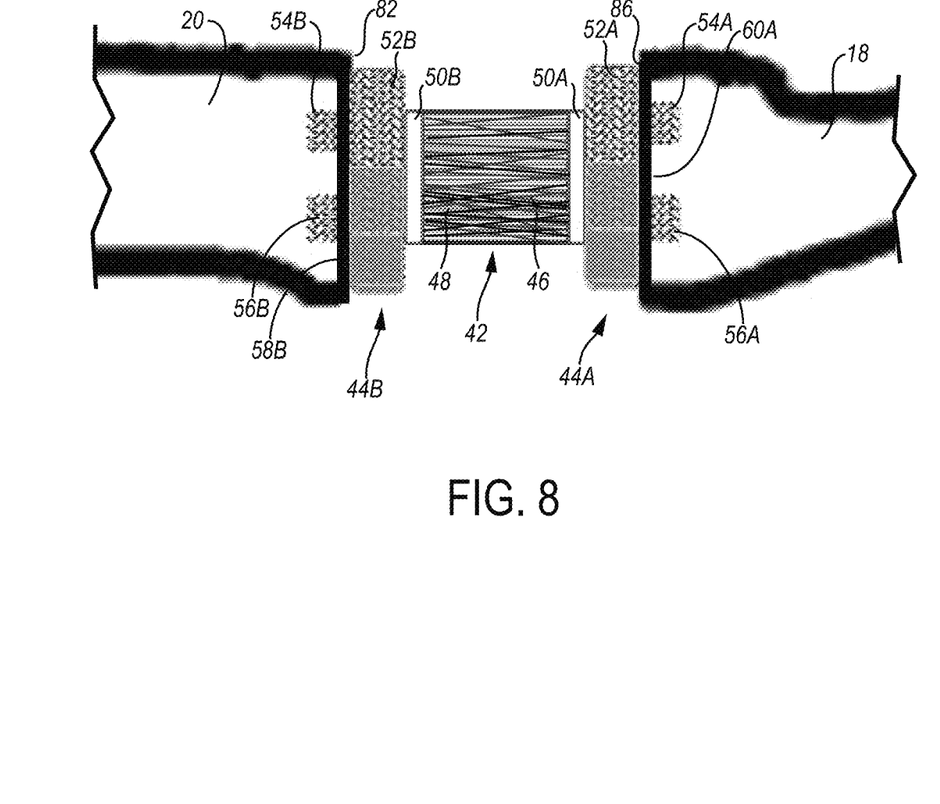
FIG. 8 is a diagram illustrating an implanted prosthetic joint device of the present disclosure implanted into the resected bone of FIG. 7.

FIG. 4 is a cross-sectional view of flexible spacer 42 of FIG. 3 showing a plurality of fibers 46 disposed in matrix 48. The size and spacing of fibers 46 relative to the depicted cross-section are not drawn to scale, and are shown for illustrative purposes. Fibers 46 can have circular cross-sectional profiles to facilitate bending, but other shapes can be used. In examples, fibers 46 can have diameters in the range of approximately 0.4 nm to approximately 100 nm. In other examples, fibers 46 can have other cross-sectional profiles. Fibers 46 can be separated from each other to provide space for matrix 48. In examples, fibers 46 can be spaced at intervals in the range of approximately 0.01 mm to approximately 2 mm. Fibers 46 can be spaced uniformly or asymmetrically or crossed. Crossing and spacing of fibers 46 can be used to adjust stiffness of flexible spacer 42. For example, as shown in FIG. 8, flexible spacer 42 can be more densely spaced near the bottom or inferior side of the device to facilitate bending in the superior direction. In an example, fibers 46 and matrix 48 can comprise polyethylene material. In examples, fibers 46 can comprise approximately 20% to approximately 70% of the area of the cross-section. Such a ratio can provide adequate stiffness to flexible spacer 42 for the purposes of compression, tension and torsion, but facilitates bending of flexible spacer 42 in a manner that realistically reproduces operation of a natural joint. Matrix 48 can comprise polymeric material that is loosely packed around and amongst fibers 46. In an example, material of matrix 48 form pseudo-tubes round fibers 46 that assist in maintaining fibers 46 separated and provide resistance to axial compressing of fibers 46, but that do not inhibit flexing of fibers 46.

FIG. 5 is a cross-sectional view of anchor component 44A of FIG. 3 showing a metallic porous structure comprised of struts 66 and voids 68. The size and spacing of struts 66 and voids 68 relative to the depicted cross-section are not drawn to scale, and are shown for illustrative purposes. struts 66 are configured to provide structural stability to anchor component 44A, while producing voids 68 that reduce the weight of component 44A and provide space for osseointegration with bone and fusion with interdigitation zone 62A (FIG. 3). In the depicted example, struts 66 and voids can reproduce the geometries of anatomic bone. In other examples, struts 66 and voids 68 can have other or synthetic geometries.

Anchor component 44A can be formed of a suitable material that promotes bone ingrowth and is biocompatible, such as porous metallic material, or a porous tantalum material having a porosity of approximately 20%-80% and pores sizes of approximately 50 μm-600 μm for example, or within any range defined between any pair of the foregoing values. An example of highly porous tantalum and titanium alloy materials are Trabecular Metal™ and OsseoTi™ generally available from Zimmer Biomet, of Warsaw, Ind. Both materials are trademarks of Zimmer Biomet.

Anchor component 44A can be formed by a plurality of different processes. In an example, such a material may be formed from a reticulated vitreous carbon foam substrate which is infiltrated and coated with a biocompatible metal, such as tantalum, by a chemical vapor deposition (CVD) process in the manner disclosed in detail in U.S. Pat. No. 5,282,861 to Kaplan, the disclosure of which is expressly incorporated herein by reference in its entirety for all purposes. In addition to tantalum, other metals such as niobium, or alloys of tantalum and niobium with one another or with other metals may also be used. The open cell metal structures can be fabricated using the tantalum metal film and carbon substrate combination, with the film deposited by CVD, which mimics bone closely in having struts 66 interconnected to form open spaces or voids 68.

In examples, anchor component 44A and other prosthetic components described herein with metallic porous structures including struts and voids and the like, such as the ones described herein, can be provided by any number of suitable three-dimensional, porous structures, and these structures can be formed with one or more of a variety of materials including but not limited to polymeric materials which are subsequently pyrolyzed, metals, metal alloys, ceramics. In some instances, a highly porous three-dimensional structure will be fabricated using a selective laser sintering (SLS) or other additive manufacturing-type process such as direct metal laser sintering. In one example, a three-dimensional porous article is produced in layer-wise fashion from a laser-fusible powder, e.g., a polymeric material powder or a single-component metal powder, that is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain embodiments, a laser selectively fuses powdered material by scanning cross-sections generated from a 3-D digital description of the article, e.g., from a CAD file or scan data, on the surface of a powder bed. Net shape and near net shape constructs are infiltrated and coated in some instances.

Complex geometries can be created using such techniques. In some instances, a three-dimensional porous structure will be particularly suited for contacting bone and/or soft tissue, and in this regard, can be useful as a bone substitute and as cell and tissue receptive material, for example, by allowing tissue to grow into the porous structure over time to enhance fixation (i.e., osseointegration) between the structure and surrounding bodily structures, for example, to provide a matrix approximating natural cancellous bone or other bony structures. In this regard, a three-dimensional porous structure, or any region thereof, may be fabricated to virtually any desired density, porosity, pore shape, and pore size (e.g., pore diameter). Such structures therefore can be isotropic or anisotropic.

Such structures can be infiltrated and coated with one or more coating materials. When coated with one or more biocompatible metals, any suitable metal may be used including any of those disclosed herein such as tantalum, titanium, a titanium alloy, cobalt chromium, cobalt chromium molybdenum, tantalum, a tantalum alloy, niobium, or alloys of tantalum and niobium with one another or with other metals. In various examples, a three-dimensional porous structure may be fabricated to have a substantial porosity, density, pore shape and/or void (pore) size throughout, or to comprise at least one of pore shape, pore size, porosity, and/or density being varied within the structure. For example, a three-dimensional porous structure to be infiltrated and coated may have a different pore shape, pore size and/or porosity at different regions, layers, and surfaces of the structure.

In some embodiments, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as titanium, a titanium alloy, cobalt chromium, cobalt chromium molybdenum, tantalum, or a tantalum alloy.

In examples, anchor component 44A can comprise titanium that is fabricated using a rapid manufacturing process. In examples, the rapid manufacturing process can comprise an additive manufacturing process, such as a powder deposition process. In such a process, very thin layers (e.g., layers that are only as thick as several levels of particles of the powdered titanium) of powdered titanium can be laid down incrementally. At each increment, selective portions of the powdered titanium can be solidified to form a portion of anchor component 44A, and the unsolidified particles can be left to support the next layer of powder. For example, a laser can be used to selectively melt portions of the powdered titanium layer that will form anchor component 44A. Subsequently, a new layer of titanium powder particles can be laid down on top of the previous, partially solidified layer and an additional solidification process can occur. The steps can be repeated until anchor component 44A is built-up from one end to the other. The unsolidified particles can then be removed. Other types of rapid manufacturing processes can be used to fabricate prosthetic joint device 40, such as 3D printing processes.

The rapid manufacturing processes can be used to include a desired level of porosity directly into anchor component 44A. Likewise, struts 66 can be made to have any desired shape, size, number and aggregate strength and density in order to generate sufficient bonding strength to survive implantation and operation of anchor component 44A, while permitting infusion of bone and polymer material from interdigitation zone 50A, as described herein.

FIG. 6 is a diagram illustrating natural anatomy 70 of first metatarsophalangeal joint 14 of FIG. 1, which can comprise proximal phalange bone 18 and metatarsal phalange bone 20. Again, as discussed above, the devices and methods described herein can be applied to other anatomies, such as metacarpal joints of a hand. Anatomy 70 can include articular cartilage pads 72A and 72B located on ends of bones 18 and 20, respectively. The joint capsule can be filled with synovial fluid 74 enclosed within synovial membrane 76. In cases of osteoarthritis ("OA"), cartilage pads 72A and 72B can become worn down and/or hardened, potentially resulting in pain and discomfort for the patient, as ends of bones 18 and 20 rub against each other. As such, it can be desirable to reproduce the natural feel and action of cartilage pads 72A and 72B with a prosthetic joint device configured according to the embodiments and examples described herein. In order to initiate an arthroplasty for metatarsophalangeal joint 14 an incision can be made through skin 78 and synovial membrane 76 to expose cartilage pads 72A and 72B. Joint 14 can be flexed to expose the opposing ends of bones 18 and 20, as shown in FIG. 7.

Figure 7:
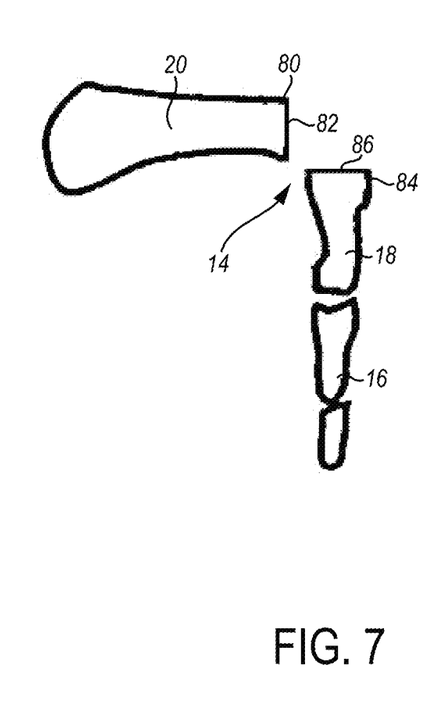
FIG. 7 is a diagram illustrating positioning of resected bones for the implantation of a prosthetic joint device of the present disclosure.

FIG. 7 is a diagram illustrating positioning of resected bones 18 and 20 for the implantation of prosthetic joint device 40 of the present disclosure into first metatarsophalangeal joint 14. Proximal phalange bone 18 can be flexed to be substantially transverse to metatarsal phalange bone 20. Distal end 80 of metatarsal phalange bone 20 can be resected to form planar anterior surface 82. Proximal end 84 of proximal phalange bone 18 can be resected to form planar posterior surface 86. As such, cartilage pads 72A and 72B can be removed and cancellous bone within bones 18 and 20 can become exposed at surfaces 82 and 86 within the hard, cortical walls of bones 18 and 20. Prosthetic joint device 40 can be flexed at flexible spacer 42 so that fixation pegs 54B and 56B can be press fit into the cancellous bone of surface 82 and fixation pegs 54A and 56A can be press fit into the cancellous bone of surface 86.

FIG. 8 is a diagram illustrating implanted prosthetic joint device 40 of the present disclosure implanted into resected bones 18 and 20 of FIG. 7. Prosthetic joint device 40 can include first anchor component 44A, second anchor component 44B and flexible spacer 42. Fixation pegs 54A and 56A of first anchor component 44A can be inserted into cancellous bone of planar posterior surface 86 such that anterior surface 60A of base 52A abuts flush against planar posterior surface 86. Fixation pegs 54B and 56B of second anchor component 44B can be inserted into cancellous bone of planar anterior surface 82 such that posterior surface 58B of base 52B abuts flush against planar anterior surface 82. Flush engagement between surface 86 and surface 60A and surface 82 and surface 58B, respectively, can facilitate stability of prosthetic joint device 40 and can promote bone ingrowth into anchor components 44A and 44B.

Prosthetic joint device 40 can be sized to fit within MPJ1 14. In examples, prosthetic joint device 40 can come in a single size that is configured to fit most or all of the different sizes of bones of the general population. In other examples, prosthetic joint device 40 can be come in a plurality of sizes, e.g., small, medium and large, to allow for semi-custom sizing. In other examples, prosthetic joint device can be custom sized for patient-specific applications, such as by measuring the size of bones 18 and 20 from preoperative imaging.

In examples, the length of prosthetic joint device 40 between surfaces 58B and 60A can be approximately equal to the length of the resected portions of bones 18 and 20 plus the thicknesses of cartilage pads 72A and 72B, such as the average of the general adult population. In examples, the diameter of bases 52A and 52B can be sized to be approximately equal to the diameter of bones 18 and 20 at joint 14, such as the average of the general adult population.

Figure 9:
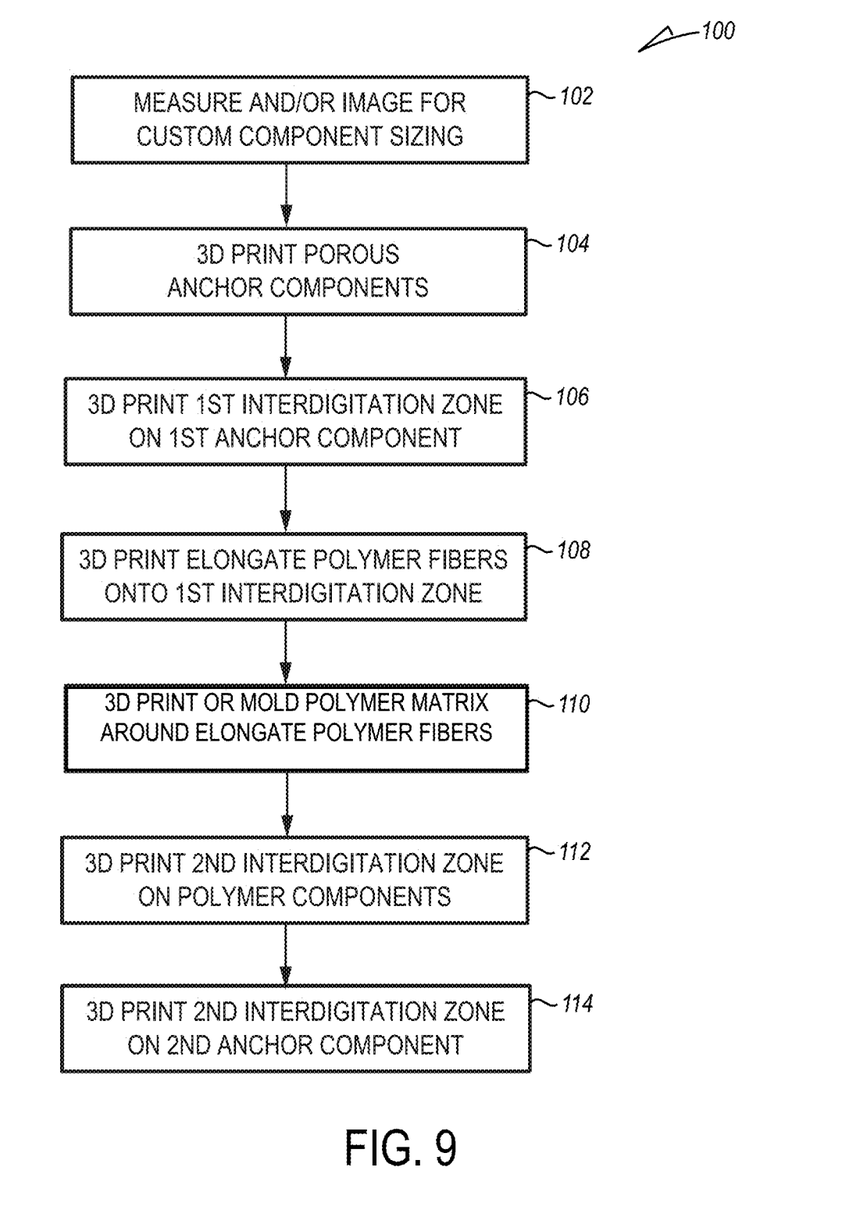
FIG. 9 is a line diagram illustrating steps of a method for manufacturing a prosthetic joint device of the present disclosure.

FIG. 9 is a line diagram illustrating steps of method 100 for manufacturing a prosthetic joint device, such as prosthetic joint device 40, of the present disclosure. At step 102, the size of joint 14 (FIG. 1) can be determined. For example, the diameters of proximal phalange bone 18 and metatarsal phalange bone 20 can be measured from pre-operative imaging of joint 14. The pre-operative imaging can include x-ray images, CT images, MRI images and the like, as well as two-dimensional and three-dimensional computer-generated models derived from the pre-operative imaging. From such measurements, the diameters for bases 52A and 52B (FIG. 3) can be determined. Additionally, the joint length, e.g., the thickness of cartilage pads 72A and 72B, can be measured. From such a measurement, the combined length of flexible spacer 42 and bases 52A and 52B can be determined. The measured size of joint 14 can be used to custom manufacture prosthetic joint device 40 to fit a specific patient, or can be used to select from a range of predetermined sizes of prosthetic joint device 40. Step 102 can be an optional step. For example, prosthetic joint device 40 can be manufactured from anatomic data of the general adult population and can be configured for use in the general adult population without measurement. In additional examples, measurement of joint 14 can be conducted intra-operatively by a surgeon or other person to determine a size from premanufactured prosthetic joint devices.

At step 104, porous anchor components 44A and 44B (FIG. 3) can be manufactured, such as by using a three-dimensional ("3D") printing process. In an example, a selective laser sintering process can be used to build up bases 52A and 52B and fixation pegs 54A-56B. Such components can include struts 66 and voids 68. Components 44A and 44B can be manufactured from a variety of materials, such as polymeric material and metallic material. Bases 52A and 52B can be made to sizes, e.g., length and diameter, based on measurements taken at step 102. In examples, components 44A and 44B are made from titanium alloys, stainless steel alloys and tantalum alloys.

At step 106, flexible spacer 42 can be manufactured, such as by using a 3D printing process or molding process or combination of both. In an example, a fused filament fabrication process can be used to build up interdigitation zones 50A and 50B, fibers 46 and matrix 48. In particular, one of interdigitation zones 50A and 50B can be directly built up on top of one of bases 52A and 52B, respectively. In such a process, for example, polymeric material of interdigitation zone 50A can be deposited onto and/or melted into voids 68 of base 52A, thereby causing adhesion of interdigitation zone 50A to base 52A. Interdigitation zone 50A can be built up to a sufficient thickness to cover or substantially the desired surface area of base 52A. As such, a planar surface of polymeric material can be built-up on base 52A to support fibers 46. In examples, interdigitation zone 50A can be made from a polymeric material, such as polyethylene. In another aspect of the present disclosure, intercalated polymer of flexible spacer 42 between two metallic scaffolds formed by porous anchor components 44A and 44B can be 3D printed using a polymer and antibiotics powder mixture. The antibiotic can be eluted out of the polymer material and from the implant into the patient to, for example, prevent and treat possible infection. The antibiotic powder can be azithromycin, amoxicillin, gentamicine or other similar medicants.

At step 108, fibers 46 can be built-up onto interdigitation zone 50A. Fibers 46 can be built integrally with interdigitation zone 50A. At step 110, material of matrix 48 can be deposited around fibers 46. Fibers 46 and matrix 48 can be simultaneously built-up on top of interdigitation zone 50A to the desired length. Fibers 46 and matrix 48 can be made to a length based on measurements taken at step 102. The material of matrix 48 can be positioned around, without attaching to, fibers 46 to facilitate flexing of flexible spacer 42. In examples, fibers 46 and matrix 48 can be made from a polymeric material, such as polyethylene. In examples, fibers 46 and matrix 48 can be made from the same or different materials as each other.

At step 112, interdigitation zone 50B can be built-up on ends of fibers 46 and on top of matrix 48. For example, a layer of the material of flexible component 42 can be formed to tie-up ends of fibers 46 and form a base for joining with second anchor component 44B. In examples, interdigitation zone 50B can be made from a polymeric material, such as polyethylene.

At step 114, interdigitation zone 50B and second anchor component 44B can be attached to each other. In an example, interdigitation zone 50B can be built-up to the desired thickness and anchor component 44B can be attached to interdigitation zone 50B, such as by being pushed into the material of interdigitation zone 50B to cause the material to penetrate into voids 68. In examples, interdigitation zone 50B can be built-up directly on base 52B and attached to fibers 46 and matrix 48.

Steps 102 through 114 describe example method steps for forming prosthetic joint devices to include a plurality of elongate fibers. Such elongate fibers can be built up in a parallel or criss-crossed axial manner to extend between anchor components. The elongate fibers can be continuous between the anchor components to provide axial or anterior-posterior strength to the device. Additionally, the elongate fibers have diameters such that the device can readily flex in the sagittal plane. The presence of matrix material alongside the elongate fibers provides stabilization to the elongate fibers to prevent buckling of the device, e.g., collapsing together of the device in the anterior-posterior direction. However, the presence of matrix material does not stiffen the device in the sagittal plane. Such a fiber and matrix composition can be produced with additive manufacturing techniques described herein. However, in other examples, manufacturing processes that can produce the fiber and matrix composition described herein can be used, such as molding processes.

Figure 10:
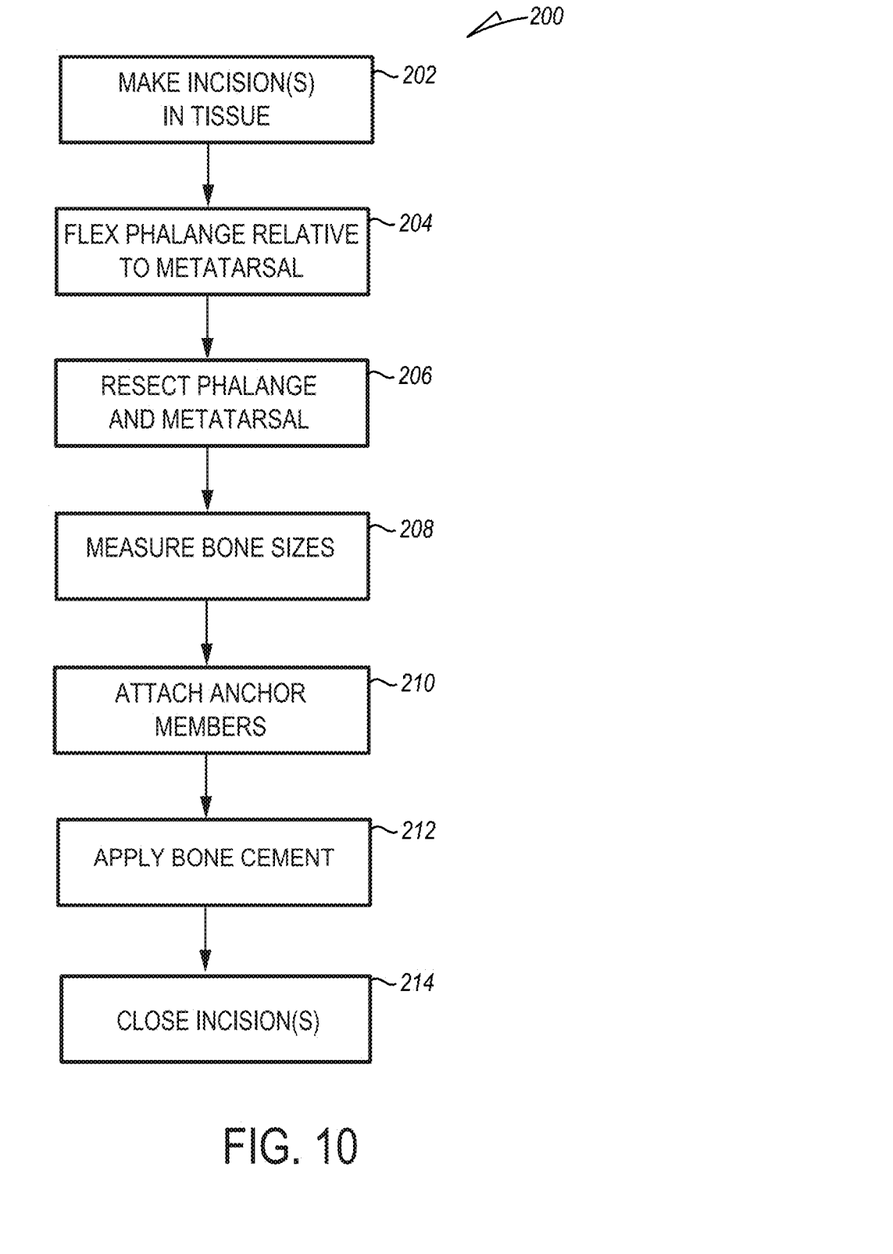
FIG. 10 is a line diagram illustrating steps of a method for implanting a prosthetic joint device of the present disclosure.

FIG. 10 is a line diagram illustrating steps of method 200 for implanting a prosthetic joint device, such as prosthetic joint device 40, of the present disclosure. Steps 202-214 provide a high-level overview of steps that can be taken to implant prosthetic joint device 40 and are not intended to be an exhaustive listing. In other examples, other steps can be used.

At step 202, incisions in tissue of the patient can be made to expose bones 18 and 20 of MTPJ1 14. Specifically, skin 78 and capsule 76 can be cut open to expose cartilage pads 72A and 72B, if said pads are not worn away from osteoarthritis, as shown in FIG. 6.

At step 204, MTPJ1 14 can be flexed by the surgeon or other personal to expose the distal ends of proximal phalange bone 18 and metatarsal phalange bone 20, as shown in FIG. 7. In such a position, cartilage pads 72A and 72B can be exposed and distal end 80 and proximal end 84 (FIG. 7) are readily viewable by the surgeon.

At step 206, bones 18 and 20 can be resected to form planar posterior surface 86 and planar anterior surface 82, respectively, as shown in FIG. 7. Bones 18 and 20 can be resected to form flat or planar surfaces against which surfaces of anchor components 44A and 44B can abut. Additionally, bones 18 and 20 can be resected to expose cancellous bone into which fixation pegs 54A-56B (FIG. 3) can be implanted.

At step 208, any desired measuring of bones 18 and 20, surfaces 86 and 82 and the gap between surfaces 86 and 82 for the sizing of the prosthetic joint component can be conducted. For example, if non-custom or standard implants are to be used, a surgeon can measure or observe the size of bones 18 and 20 intraoperatively to determine which size of prosthetic joint device 40 is to be used from a set of standard sized devices.

At step 210, any anchor members of prosthetic joint device 40 can be connected to bones 18 and 20. For example, as shown in FIG. 8, fixation pegs 54A and 56A of anchor component 44A can be inserted into cancellous bone at surface 86 at bone 18, and fixation pegs 54B and 56B of anchor component 44B can be inserted into cancellous bone as surface 82 of bone 20. Flexible spacer 42 can be flexed or bent by the surgeon to simultaneously attach all of fixation pegs 54A-56B. Thereafter, tension on flexible spacer can be released and fibers 46 of flexible spacer can relax and return to the natural unflexed condition so that bone 18 can be moved into axial alignment with bone 20, as shown in FIG. 8.

At step 212, any bone cement can be applied to anchor components 44A and 44B if desired. Application of bone cement can be optional if a surgeon can determine that adequate bone material exists to support fixation pegs 54A-56B. Likewise, any other observations of the fit of prosthetic joint device 40 or the flexion of the repaired joint 14 can be observed and evaluated after implantation.

At step 214, any incisions made at step 202 can be closed-up, if desired or deemed appropriate by the surgeon.

Figure 11:
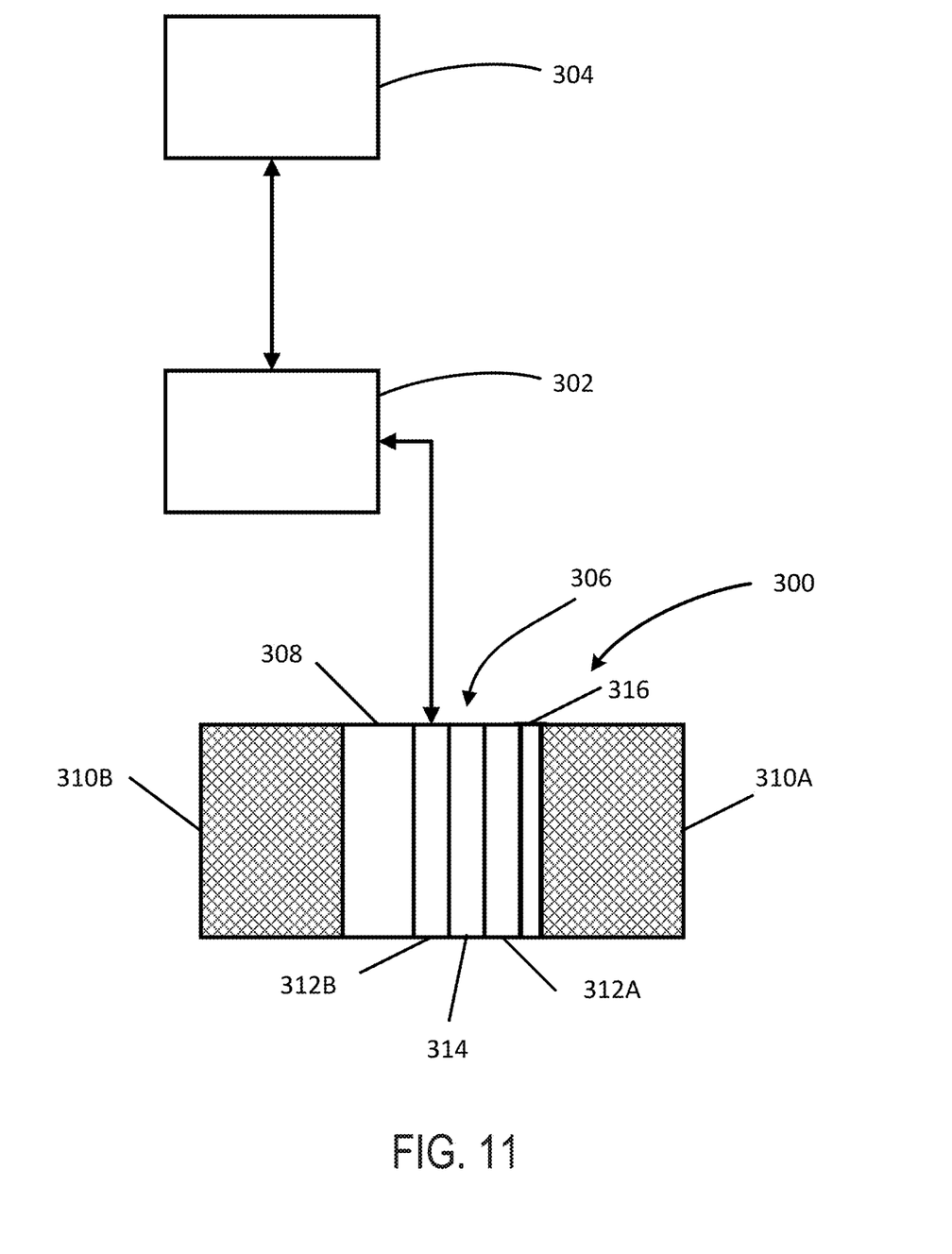
FIG. 11 is a schematic diagram illustrating a prosthetic joint implant of the present disclosure including an electric circuit.

FIG. 11 is a schematic diagram illustrating prosthetic joint implant 300 of the present disclosure including electronic circuit 306. Electronic circuit 306 can be in communication with reader 302 and computer system 304. Prosthetic joint implant 300 can comprise polymer layer 308 disposed between porous scaffolds 310A and 310B. Electronic circuit 306 can comprise capacitor layers 312A and 312B, insulator 314 and resistor 316. Components of prosthetic joint implant 300 are not drawn to scale.

Porous scaffolds 310A and 310B and polymer layer 308 can be configured according to the devices described herein. Electronic circuit 306 can comprise an active version of a prosthetic joint implant that can communicate information from the patient. Electronic circuit 306 can include one or more capacitors formed by capacitor layers 312A and 312B and insulator 314, as well as one or more of resistor 316 and other electronic components. The electronic components can be 3D printed onto the interfaces between metallic porous scaffolds 310A and 310B and polymer layer 308 to measure stresses and strains during activities of daily living. Capacitor layers 312A and 312B can comprise conducting plates that can be made of tantalum, silver or niobium, while insulator 314 can comprise a dielectric that can be made of polymer or ceramic materials. Resistor 316 can be printed from carbon and ceramic powders.

Information or data relating to the measurements taken by electronic circuit 306 can be transmitted to reader 302. Reader 302 can be configured to wirelessly communicate with electronic circuit 306. In examples, reader 302 can additionally have writing capabilities to send information to electronic circuit 306. In such cases, electronic circuit 306 can include a receiver and an electronic memory device. As such, patient-specific information can be written to prosthetic joint implant 300. Information obtained from electronic circuit 306 can be transmitted to computer system 304 where the data can be stored and analyzed. The stresses and strains can be analyzed to determine the condition of prosthetic joint implant 300 and to evaluate the lifestyle of the patient.

VARIOUS NOTES & EXAMPLES

Example 1 can include or use subject matter such as a device for the repair of a phalangeal joint that can comprise a first anchor, a second anchor and a flexible spacer connecting the first anchor and the second anchor. The flexible spacer can comprise a plurality of elongate fibers extending between the first and second anchors, and a polymeric matrix interspersed with the plurality of elongate fibers.

Example 2 can include, or can optionally be combined with the subject matter of Example 1, to optionally include a flexible spacer and first and second anchors that can be integral with each other.

Example 3 can include, or can optionally be combined with the subject matter of one or any combination of Examples 1 or 2 to optionally include the first anchor and the second anchor that can be comprised of a porous structure.

Example 4 can include, or can optionally be combined with the subject matter of one or any combination of Examples 1 through 3 to optionally include the first anchor being connected to a first end of the flexible spacer via a first interdigitation zone transitioning the porous structure of the first anchor into the plurality of elongate fibers and polymeric matrix of the flexible spacer; and the second anchor being connected to a second end of the flexible spacer via a second interdigitation zone transitioning the porous structure of the second anchor into the plurality of elongate fibers and polymeric matrix of the flexible spacer.

Example 5 can include, or can optionally be combined with the subject matter of one or any combination of Examples 1 through 4 to optionally include the first and second interdigitation zones extending into pores of the first and second anchors and are free of fibers of the plurality of elongate fibers.

Example 6 can include, or can optionally be combined with the subject matter of one or any combination of Examples 1 through 5 to optionally include the flexible spacer being comprised of a polymeric composition and the first and second anchors are comprised of porous metallic structures.

Example 7 can include, or can optionally be combined with the subject matter of one or any combination of Examples 1 through 6 to optionally include the flexible spacer comprising fibers of the plurality of fibers in the range of approximately 20% to approximately 70% of the volume of the flexible spacer.

Example 8 can include, or can optionally be combined with the subject matter of one or any combination of Examples 1 through 7 to optionally include the first anchor and the second anchor each including one or more fixation pegs.

Example 9 can include, or can optionally be combined with the subject matter of one or any combination of Examples 1 through 8 to optionally include fibers of the plurality of elongate fibers that are spaced apart from each other by the polymeric matrix.

Example 10 can include, or can optionally be combined with the subject matter of one or any combination of Examples 1 through 9 to optionally include fibers of the plurality of fibers extending parallel to center axes of the first anchor and the second anchor in an unflexed condition.

Example 11 can include, or can optionally be combined with the subject matter of one or any combination of Examples 1 through 10 to optionally include fibers of the plurality of fibers extend criss-crossed relative to each other and center axes of the first anchor and the second anchor in an unflexed condition.

Example 12 can include or use subject matter such as a prosthetic metatarsophalangeal joint device that can comprise a metatarsal bone anchor that can comprise a porous metallic material, a phalangeal bone anchor that can comprise a porous metallic material, and a polymeric spacer element that can connect the metatarsal bone anchor and the phalangeal bone anchor, the polymeric spacer element can comprise a plurality of elongate fibers extending between the metatarsal bone anchor and the phalangeal bone anchor.

Example 13 can include, or can optionally be combined with the subject matter of Example 12, to optionally include first and second fixation pegs extending from the metatarsal bone anchor and the phalangeal bone anchor, respectively, a polymeric matrix material interspersed with fibers of the plurality of elongate fibers, and interdigitation zones fusing struts of the porous metallic material of the metatarsal bone anchor and the phalangeal bone anchor with the fibers of the plurality of elongate fibers.

Example 14 can include or use subject matter such as a method of manufacturing a device for the repair of a phalangeal joint. The method can comprise fabricating first and second anchor components using a first additive manufacturing process to produce a porous structure within each component, fabricating a flexible spacer component using a second additive manufacturing process or a molding process to produce a plurality of elongate fibers extending across the flexible spacer, and attaching opposing ends of the flexible spacer component to the first and second anchor components.

Example 15 can include, or can optionally be combined with the subject matter of Example 14, to optionally include fabricating the first and second anchor components using the first additive manufacturing process and fabricating the flexible spacer component using the second additive manufacturing process or the molding process by printing the components from different materials.

Example 16 can include, or can optionally be combined with the subject matter of one or any combination of Examples 14 or 15 to optionally include printing the first and second anchor components by selective laser sintering or electron beam based three-dimensional printing the first and second metallic porous anchor components from a metallic powder.

Example 17 can include, or can optionally be combined with the subject matter of one or any combination of Examples 14 through 16 to optionally include fabricating the flexible spacer component using the second additive manufacturing process by three-dimensionally printing or molding the flexible spacer from polyethylene.

Example 18 can include, or can optionally be combined with the subject matter of one or any combination of Examples 14 through 17 to optionally include fabricating a flexible spacer component using a second additive manufacturing process or a molding process to produce a plurality of elongate fibers extending across the flexible spacer by extending the fibers straight across or extending the fibers across in a criss-cross manner.

Example 19 can include, or can optionally be combined with the subject matter of one or any combination of Examples 14 through 18 to optionally include fabricating the flexible spacer component using the second additive manufacturing process or the molding process by fusing a first interdigitation zone into the first anchor component, building a plurality of elongate fibers out of the interdigitation zone, interspersing a matrix layer between fibers of the plurality of fibers, building a second interdigitation zone onto the plurality of elongate fibers and the matrix layer, and fusing the second interdigitation zone into the second anchor component.

Example 20 can include, or can optionally be combined with the subject matter of one or any combination of Examples 14 through 19 to optionally include fabricating the first and second anchor components using the first additive manufacturing process to produce the porous structure within each component by producing a plurality of struts interconnected to form open spaces.

Example 21 can include, or can optionally be combined with the subject matter of one or any combinations of Examples 14 through 20 to optionally include fabricating the flexible spacer component using the second additive manufacturing process by three-dimensionally printing or molding the flexible spacer to include an antibiotic powder.

Example 22 can include, or can optionally be combined with the subject matter of one or any combinations of Examples 14 through 21 to optionally include fabricating the flexible spacer component using the second additive manufacturing process by three-dimensionally printing or molding the flexible spacer to include an electronic circuit.

Example 23 can include, or can optionally be combined with the subject matter of one or any combinations of Examples 14 through 22 to optionally include fabricating the flexible spacer component using the second additive manufacturing process by three-dimensionally printing or molding the flexible spacer to include an electronic circuit that can measure stress and strain in the device. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A prosthetic metatarsophalangeal joint device for the repair of a metatarsophalangeal joint, the device comprising:
    a metatarsal anchor comprising a porous structure;
    a phalangeal anchor comprising a porous structure; and
    a flexible spacer connecting the metatarsal anchor and the phalangeal anchor, the flexible spacer comprising:
        a plurality of elongate fibers extending between the metatarsal and phalangeal anchors; and
        a polymeric matrix interspersed with the plurality of elongate fibers,
    wherein:
        the metatarsal anchor is connected to a first end of the flexible spacer via a first interdigitation zone transitioning the porous structure of the metatarsal anchor into the plurality of elongate fibers and polymeric matrix of the flexible spacer;
        the phalangeal anchor is connected to a second end of the flexible spacer via a second interdigitation zone transitioning the porous structure of the phalangeal anchor into the plurality of elongate fibers and polymeric matrix of the flexible spacer; and
        the first and second interdigitation zones extend into pores of the metatarsal and phalangeal anchors and are free of fibers of the plurality of elongate fibers.

2. The prosthetic metatarsophalangeal joint device of claim 1, wherein the flexible spacer and the metatarsal and phalangeal anchors are integral with each other.

3. The prosthetic metatarsophalangeal joint device of claim 1, wherein the flexible spacer is comprised of a polymeric composition and the porous structures of the metatarsal and phalangeal anchors are comprised of porous metallic material.

4. The prosthetic metatarsophalangeal joint device of claim 1, wherein the flexible spacer comprises fibers of the plurality of fibers in the range of approximately 20% to approximately 70% of the volume of the flexible spacer.

5. The prosthetic metatarsophalangeal joint device of claim 1, wherein the metatarsal anchor and the phalangeal anchor each include one or more fixation pegs.

6. The prosthetic metatarsophalangeal joint device of claim 1, wherein fibers of the plurality of elongate fibers are spaced apart from each other by the polymeric matrix.

7. The prosthetic metatarsophalangeal joint device of claim 1, wherein fibers of the plurality of fibers extend parallel to center axes of the metatarsal anchor and the phalangeal anchor in an unflexed condition.

8. The prosthetic metatarsophalangeal joint device of claim 1, wherein fibers of the plurality of fibers extend criss-crossed relative to each other and center axes of the metatarsal anchor and the phalangeal anchor in an unflexed condition.

9. A prosthetic metatarsophalangeal joint device comprising:
 a metatarsal bone anchor comprising a porous metallic material;
 a phalangeal bone anchor comprising a porous metallic material; and
 a polymeric spacer element connecting the metatarsal bone anchor and the phalangeal bone anchor, the polymeric spacer element comprising a plurality of elongate fibers extending between the metatarsal bone anchor and the phalangeal bone anchor and a polymeric matrix material interspersed with fibers of the plurality of elongate fibers,
 wherein:
  the metatarsal bone anchor is connected to a first end of the polymeric spacer element via a first interdigitation zone transitioning the porous metallic structure of the metatarsal bone anchor into the plurality of elongate fibers and polymeric matrix of the polymeric spacer element;
  the phalangeal bone anchor is connected to a second end of the polymeric spacer element via a second interdigitation zone transitioning the porous metallic structure of the phalangeal bone anchor into the plurality of elongate fibers and polymeric matrix of the polymeric spacer element; and
  the first and second interdigitation zones extend into pores of the metatarsal and phalangeal bone anchors and are free of fibers of the plurality of elongate fibers.

10. The prosthetic metatarsophalangeal joint device of claim 9, further comprising:
 first and second fixation pegs extending from the metatarsal bone anchor and the phalangeal bone anchor, respectively;
 wherein the first and second interdigitation zones fuse struts of the porous metallic material of the metatarsal bone anchor and the phalangeal bone anchor with the fibers of the plurality of elongate fibers.

* * * * *